United States Patent
Smuda

(10) Patent No.: US 6,239,310 B1
(45) Date of Patent: May 29, 2001

(54) METHOD OF RECOVERY OF TEREPHTHALIC ACID AND ETHYLENE GLYCOL FROM POLY/ETHYLENE TEREPHTHALATE/WASTES

(76) Inventor: Heinrich Smuda, Ben Gurion-Ring, D-60437 Frankfurt am Main (DE)

( * ) Notice: Subject to any disclaimer, the term of this patent is extended or adjusted under 35 U.S.C. 154(b) by 0 days.

(21) Appl. No.: 09/355,322
(22) PCT Filed: Dec. 2, 1997
(86) PCT No.: PCT/IB97/01497
  § 371 Date: Aug. 2, 1999
  § 102(e) Date: Aug. 2, 1999
(87) PCT Pub. No.: WO99/28285
  PCT Pub. Date: Jun. 10, 1999
(51) Int. Cl.⁷ .............................. C07C 51/00; C07C 51/42
(52) U.S. Cl. ........................... 562/487; 562/483; 562/485
(58) Field of Search ..................................... 562/483, 485, 562/487

(56) References Cited

U.S. PATENT DOCUMENTS 5,545,746 * 8/1996 Benzaria et al. .

FOREIGN PATENT DOCUMENTS

839371 * 6/1960 (GB) .
163385 * 9/1988 (IN) .

* cited by examiner

Primary Examiner—Paul J. Killos
(74) Attorney, Agent, or Firm—Arent Fox Kintner Plotkin & Kahn, PLLC

(57) ABSTRACT

A subject of the invention is the method of recovery of terephthalic acid and ethylene glycol from poly/ethylene terephthalate/wastes. According to the invention poly/ethylene terephthalate/ is heated in an aqueous solution at the temperature from 150° C. to 280° C. with a reagent substance, chosen from the group, comprising bicarbonates of ammonia and alkali metals, ammonium carbamate and urea, which substances are used in amounts not less than a stoechiometric amount.

3 Claims, No Drawings

METHOD OF RECOVERY OF TEREPHTHALIC ACID AND ETHYLENE GLYCOL FROM POLY/ETHYLENE TEREPHTHALATE/WASTES

Subject of the invention is the method of recovery of terephtalic acid and ethylene glycol from poly/ethylene terephtalate/ waste.

Still growing global production of poly/ethylene terephtalate/, which is used as a popular material for the production of bottles and containers, industrial shapes, synthetic fibres, insulation foils and other everyday use articles, causes, besides its numerous utility values, a fast increase of its wastes amount.

The chemical nature of poly/ethylene terephtalate/ causes that as a plastic of an extraordinary high resistance against the extremely severe atmospheric conditions, the wastes do not yield to microbiological degradation and a natural decomposition and they last, occupying in the unchanged form and being very noxious and durable pollution of the environment.

At the same time the raw materials for a production of poly/ethylene terephtalate/, i.e. ethylene glycol and terephtalic acid are still expensive.

The manufacture of poly/ethylene terephtalate/ waste for the regranulate, which is then added to the principal raw material in a process of forming any products does not solve the waste problem and similarly, as its harmful combustion, it is a stopgap.

Till now, from the American patent description no. 4.542239 a process of recovery terephtalic acid from poly/ethylene terephtalate/ is known, which is based on a reaction of suitably disintegrated wastes, comprising used containers and bottles of beverages, with a medium, containing ammonium hydroxide at the increased temperature and an increased pressure, and then the acidification of formed aqueous solution of water-soluble diammonium salt of terephtalic acid to precipitate terephtalic acid. A part of the solution remained after separation of terephtalic acid was subjected to the treatment with alkaline medium to separate ammonium, which was recycled together with a second part of the solution, remained after separation of terephtalic acid, as the charge material in a consequent part of substrates.

From the German patent application no. 19629042.2 a method of production terephtalic acid and ethylene glycol from poly/ethylene terephtalate/ waste is known. The process is carried in a slightly alkaline medium of carbonates of the I-st group metals or ammonium carbonate, by the decreased pH value, which does not allow any undesired side reactions and prevents the contamination of products.

In a known method suitably disintegrated poly/ethylene terephtalate/ wastes are subjected to the operation of an aqueous solution of alkali metal or ammonia carbonate while the temperature is increased gradually, preferably up to 200° C., and then the temperature is kept constant till the digestion of polyester is completed. Carbon dioxide, formed during the reaction is permanently carried away from the reaction environment under a constant pressure and is absorbed in an aqueous solution of alkali metal hydroxide, preferably of sodium Na, potassium K or ammonia water till the saturation moment. A reaction mixture, after separation of solid impurities and cooling, is then subjected to an oxidation process, preferably in aqueous solution of hydrogen peroxide of a concentration of 3% b.w., and then the solution is neutralised with an acid solution, preferably mineral acid solution, till the precipitation of terephtalic acid is completed. From a resulted suspension of terephtalic acid in a solution of ethylene glycol and salt of an acid used for the neutralisation a solid phase is separated, which is then subjected to the purification process, including washing and/or crystallisation and drying, which gives in a result terephtalic acid of a desired water content. Ethylene glycol is distilled off from the resulted solution, after evaporation of water and separation the salt of an acid used for neutralisation. Carbonate, formed in a result of absorption of educed carbon dioxide in hydroxide or ammonia solution is then used in a consequent batch, processed according to the known method.

In the method according to the invention, disintegrated poly/ethylene terephtalate/ wastes are heated with a reagent substance, chosen from the group, comprising bicarbonates of ammonia and alkali metals, ammonium carbamate and urea, which substances are used in an aqueous solution in amounts not less than a stechiometric amount at a temperature between 150°–280° C.

After the poly/ethylene terephtalate/ is digested a resulted aqueous solution of terephtalic acid salts is subjected to the further processing according to a method known from the German patent application no. 19629042.2, comprising filtering of a hot solution, neutralisation of a filtrate with a mineral acid, separation of terephtalic acid, washing of terephtalic acid with water and the eventual crystallisation from water, a neutralisation resulted filtrate and separation of ethylene glycol using distillation or extraction.

The preferable course of the reaction carried using a method according to the invention results at the temperatures range between 180–200° C.

The method according to the invention enables a production of high purity products demanded by the market and it gives a possibility of utilisation of wastes, being the durable and noxious pollution of a natural environment.

EXAMPLE I

In a heated autoclave, provided with a mixer and filled partially with water, cut poly/ethyleneterephtalate/ wastes in a form of scraps of foil and pieces of industrial shapes were placed in the amount of 1000 g together with a solution of 875 g of sodium bicarbonate ($NaHCO_3$) in 10 liters of water, and then a content of the reactor was heated up to 200° C. and the temperature was kept till the digestion of poly/ethylene terephtalate/ was completed and the formation of carbon dioxide was stopped. Then the autoclave was relieved and carbon dioxide and water excess were separated, then a resulted solution was filtered hot through a filter with active carbon. The filtrate was neutralised with hydrochloric acid and a precipitate of terephtalic acid was separated from a reaction solution using a centrifuge. The resulted product was washed with a distilled water and crystallised from water, giving 864 g of terephtalic acid. At the same time ethylene glycol was separated from the neutralised filtrate using extraction with diethylcarbonate, obtaining 322,6 g of ethylene glycol.

EXAMPLE II

In a heated autoclave, provided with a mixer and filled partially with water, disintegrated poly/ethyleneterephtalate/ wastes in a form of scraps of bottles and textiles were placed in the amount of 1000 g together with a solution of 1043 g of potassium bicarbonate ($KHCO_3$) in 10 liters of water, and then a content of the reactor was heated up to 190° C. and the temperature was kept till the digestion of poly/ethylene terephtalate/ was completed and the formation of carbon dioxide was stopped. Then the autoclave was relieved and carbon dioxide was separated, and a resulted solution was filtered hot through a filter with active carbon. The filtrate was neutralised with orthophosphoric acid and a precipitate of terephtalic acid was separated from a reaction solution using a centrifuge. The resulted product was washed with a distilled water and crystallised from water, giving 864,2 g of terephtalic acid. At the same time ethylene glycol was separated from the neutralised filtrate using distillation, obtaining 322,5 g of ethylene glycol and almost theoretical amount of inorganic salt.

EXAMPLE III

In a heated autoclave, provided with a mixer and filled partially with water, disintegrated poly/ethyleneterephtalate/ wastes in a form of scraps of film and bottles were placed in the amount of 1000 g together with a solution of 823 g of ammonium bicarbonate ($NH_4HCO_3$) in 10 liters of water. Then a content of the reactor was heated up to 185° C. and the temperature was kept till the digestion of poly/ethylene terephtalate/ was completed and the formation of carbon dioxide was stopped. The autoclave was relieved and the excess of carbon dioxide and water were removed and then carbon dioxide was absorbed in a reactor, containing ammonia solution. The yielded in a reactor ammonium bicarbonate was used in the next batch in preparation the input mixture. The water solution of products formed in the autoclave was filtered hot through a filter with active carbon. The chilled filtrate was acidified with sulphuric acid and a precipitated deposit of terephtalic acid was separated from the reaction liquor in a centrifuge. The resulted product was washed with a distilled water and crystallised from water, giving 863 g of terephtalic acid. From the solution, after precipitate of terephtalic acid and evaporation of a solvent, ethylene glycol in amount of 322 g and a theoretical amount of ammonium salt were obtained.

EXAMPLE IV

In a heated autoclave, provided with a mixer and filled partially with water, disintegrated poly/ethyleneterephtalate/ wastes in a form of scraps of film and bottles in the amount of 1000 g were placed together with a solution of 407 g of ammonium carbamate ($NH_4CONH_2$) in 10 liters of water. Then a content of the reactor was heated up to 200° C. and the temperature was kept till the digestion of poly/ethylene terephtalate/. The autoclave was relieved and the excess of carbon dioxide and water were removed. The water solution of products formed in the autoclave was filtered hot through a filter with active carbon. The chilled filtrate was acidified with sulphuric acid and the precipite of terephtalic acid was separated from a filtrate in a centrifuge. The resulted product was washed with distilled water, giving 862 g of terephtalic acid. From a solution, resulted after precipitation and separation ethylene glycol in amount of 321 g was separated, using distillation process, and the residue was ammonium sulphate.

EXAMPLE V

In a heated autoclave, provided with a mixer and filled partially with water, disintegrated poly/ethyleneterephtalate/ wastes in a form of synthetic fibre postproduction waste were placed in the amount of 1000 g together with a solution of 313 g urea ($NH_2COHN_2$) in a form of a solution in 10 liters of water. Then a content of the reactor was heated up to 200° C. and the temperature was kept till the digestion of poly/ethylene terephtalate/ was completed and then it was filtered hot through a filter. The chilled filtrate was subjected to a neutralisation with sulphuric acid and the precipitated terephtalic acid was separated in a centrifuge and washed and crystallised, giving 864 g of a product. Ethylene glycol in amount of 322 g was obtained from the remained solution and then in a result of a crystallisation ammonium sulphate was separated.

The mutual amounts of substrates and products, calculated on 1000 parts b.w. of poly/ethylene terephtalate/ in the examples is presented in a table no. 1.

TABLE 1

| | Per 1000 parts b.w. of poly/ethylene terephtalate | | | | |
|---|---|---|---|---|---|
| | example I | example II | example III | example IV | example V |
| Reagent | $NaHCO_3$ 875 | $KHCO_3$ 1043 | $NH_4HCO_3$ 823 | $NH_4CONH_2$ 407 | $NH_2CONH_2$ 313 |
| water as reagent | — | — | — | 187,5 | 281,5 |
| amount of educed $CO_2$ /calculated/ | 458 | 458 | 458 | 230 | 230 |
| Terephtalic acid | 864 | 864,2 | 863 | 862 | 864 |
| Ethylene glycol | 322,6 | 322,5 | 322,5 | 321,0 | 322,0 |

The result of chemical analysis of terephtalic acid, obtained in the above examples are presented in a table no. 2.

TABLE 2

| | Example no. | | | | |
|---|---|---|---|---|---|
| Result of analysis | I | II | III | IV | V |
| acid number [mg KOH/g] | 675,1 | 675,0 | 674,9 | 675,1 | 675,2 |
| sodium Na* [ppm] | 5,62 | 1,80 | 1,76 | 1,80 | 1,50 |
| potassium K* [ppm] | 1,10 | 3,9 | 1,32 | 1,10 | 1,11 |
| 4-CBA content [ppm] | 18,10 | 18,00 | 16,30 | 15,40 | 15,80 |
| p-toluic acid content [ppm] | 18,2 | 28,1 | 36,0 | 18,5 | 18,2 |
| benzoic acid content [ppm] | 10,6 | 10,5 | 10,3 | 11,2 | 9,5 |

What is claimed is:
1. The method of recovery of terephtalic acid and ethylene glycol from poly/ethylene terephtalate/ wastes, in which the suitably disintegrated wastes of poly/ethylene terephtalate/ are subjected to the treatment of an aqueous, slightly alkaline solution at the increased temperature, and then the reaction mixture, after separation solid impurities and chilling, is neutralised with acid and from the resulted mixture a solid phase is separated, which is subjected to the purification and drying, and from the remained solution ethylene glycol is separated, characterised in, that poly/ethylene terephtalate/ is heated in an aqueous solution at the temperatures from 150° C. to 280° C. with a reagent substance, chosen from the group, comprising bicarbonates of ammonia and alkali metals, ammonium carbamate and urea, which substances are used in amounts not less than a stechiometric amount.

2. The method according to the claim no. 1, characterised in, that disintegrated poly/ethylene terephtalate/ is heated in an aqueous solution at the temperatures between 180° C. and 200° C.

3. The method according to claim 1, characterised in, that carbon dioxide formed during in a process is at least partially absorbed in an alkali solution and recycled.

* * * * *